(12) United States Patent
Zaleski

(10) Patent No.: US 6,520,929 B2
(45) Date of Patent: *Feb. 18, 2003

(54) INFUSION SLEEVE FOR OPHTHALMIC SURGERY

(75) Inventor: Ed Zaleski, Santa Ana, CA (US)

(73) Assignee: Advanced Medical Optics, Santa Ana, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/552,826

(22) Filed: Apr. 20, 2000

(65) Prior Publication Data

US 2001/0034504 A1 Oct. 25, 2001

(51) Int. Cl.⁷ .................................................. A61M 3/00
(52) U.S. Cl. ........................................ 604/44; 606/107
(58) Field of Search .............................. 604/22, 27, 35, 604/40, 43, 44, 48, 158, 164.01, 264, 272, 289–291, 294, 521, 164.02, 164.11, 164.12, 166.01; 606/107, 167, 169–171

(56) References Cited

U.S. PATENT DOCUMENTS

| 4,428,748 A | | 1/1984 | Peyman et al. ................ 604/22 |
| 4,808,154 A | * | 2/1989 | Freeman ........................ 604/22 |
| 5,151,083 A | * | 9/1992 | Pichler ......................... 604/19 |
| 5,269,291 A | * | 12/1993 | Carter | |
| 5,505,693 A | | 4/1996 | Mackool ....................... 604/22 |
| 5,685,841 A | | 11/1997 | Mackool ....................... 604/22 |
| 5,807,310 A | | 9/1998 | Hood ........................... 604/22 |
| 5,941,887 A | * | 8/1999 | Steen et al. .................. 606/107 |
| 5,984,889 A | * | 11/1999 | Christ et al. .................. 604/22 |
| 5,984,904 A | * | 11/1999 | Steen et al. | |
| 6,033,376 A | | 3/2000 | Rockley ....................... 604/22 |
| 6,117,151 A | | 9/2000 | Urich et al. ................. 606/169 |

FOREIGN PATENT DOCUMENTS

| WO | PCT/AU95/00558 | 8/1995 | ............ A61F/9/00 |
| WO | PCT/US97/22028 | 12/1997 | |

* cited by examiner

*Primary Examiner*—Brian L. Casler
*Assistant Examiner*—LoAn H. Thanh
(74) *Attorney, Agent, or Firm*—Walter A. Hackler; Peter Jon Gluck

(57) ABSTRACT

Sleeve apparatus for a phacoemulsification/irrigation and aspiration handpiece includes an elongate sleeve having a proximal and a distal end with a sleeve establishing an annular passage around a needle enabling irrigation fluid to pass into the eye through the passage and into the eye while cooling the needle. The elongate sleeve includes a hub disposed a proximal end for enabling attachment of the sleeve to the handpiece and a port disposed approximate the distal end and in fluid communication with the annular passage is provided for introducing irrigation fluid into the eye. An Internal circumferential berm, disposed between the port and the distal end is provided to reduce flow of the irrigation fluid therepast, to provide rigidity to the distal end of the sleeve and concomitantly provide limited contact with the needle in order to produce thermal transfer therebetween.

1 Claim, 1 Drawing Sheet

INFUSION SLEEVE FOR OPHTHALMIC SURGERY

The present invention is generally related to phacoemulsification handpieces for the removal of cataract lens from an eye, and is more particularly related to sleeve apparatus for phacoemulsification handpiece.

A well known method for the removal of a cataract through a surgical incision in the eye is now phacoemulsification. A handpiece for phacoemulsification generally includes an ultrasonic generator which is attached to a hollow needle. Vibration of the needle by the generator is used to emulsify lens tissue and aspiration of the emulsified lens tissue, and is effected through a lumen in the needle.

The needle is surrounded by a sleeve when inserted through an incision in the eye, and a needle tip engages and emulsifies the cataract while suction is applied to the needle lumen to withdraw the emulsified cataract through the needle and out of the eye.

The infusion sleeve is typically made from silicone, which provides a desired flexibility for fluid sealing at the handpiece interface and with eye tissue. The sleeve therefore protects the wound through which the needle is passed from contacting the needle which can become heated. Additionally, the sleeve establishes an annular passage around the needle for providing irrigation fluid to the eye while at the same time cooling the needle. It is important that the sleeve tip be sufficiently rigid to withstand insertion through the wound entry into the eye.

The present invention is directed to an infusion sleeve, which provides enhanced rigidity to facilitate insertion into an eye wound. In addition, fluid flow with the irrigation fluid is controlled by the sleeve in order to minimize fluid flow between the sleeve tip and the phacoemulsificaiton needle.

SUMMARY OF THE INVENTION

Sleeve apparatus in accordance with the present invention for a phacoemulsificaiton/irrigation and aspiration handpiece, generally includes an elongate sleeve, having a proximal and a distal end. The sleeve has a larger diameter than a needle passing therethrough and accordingly establishes an annular passage around the needle, which enables irrigation fluid to flow therethrough the annular passage and a cornea/sclera wound. Thus, the irrigation fluid passing over the needle provides cooling.

The elongate sleeve includes a hub disposed at the proximal end for enabling the attachment of the sleeve to the handpiece. A port, disposed proximate the distal, is provided for introducing the irrigation fluid into the eye.

An internal circumferential berm is disposed between the port and the distal end in order to reduce the flow of irritation fluid therepast, provide rigidity to the proximal end and concomitantly provide limited contact with the needle in order to reduce thermal transfer therebetween.

More particularly, the berm has a length measured along a longitudinal axis of the sleeve, which is less than a distance between the port and the distal end. This reduced distance is provided to minimize contact and reduce heat transfer. The berm may have a length which is approximately equal to a distance between the port and the distal end. This may be provided in order to further limit the amount of fluid flow therepast and enhance the flow of fluid through the port for irrigation purposes.

Alternately, the sleeve apparatus in accordance with the present invention, may include an elongate sleeve, having a hub disposed at the proximal end for enabling attachment of the sleeve to the handpiece, and a port disposed proximate the distal end in fluid communication with the annular passage for introducing the irrigation fluid to the eye. The elongate sleeve may include a first diameter between the proximal end and the port and a second diameter between the port and the distal end with the second diameter being smaller that the first diameter.

In this instance, the second diameter is sized for reducing flow of irrigation fluid therepast in order to increase flow of irrigation fluid through the port. For example, the second diameter may have a length, measured along the longitudinal axis of the sleeve, which is less than a distance between the port and the distal end in order to reduce thermal transfer between the sleeve and needle.

Alternatively considered, the elongate sleeve may be provided with a first wall thickness between the proximal end and the port and a second wall thickness between the port and the distal end with the second wall thickness being greater that the first wall thickness.

BRIEF DESCRIPTION OF THE DRAWINGS

The present invention may be more clearly appreciated when taken in conjunction with the accompanying drawings in which.

DETAILED DESCRIPTION

Figure 1:
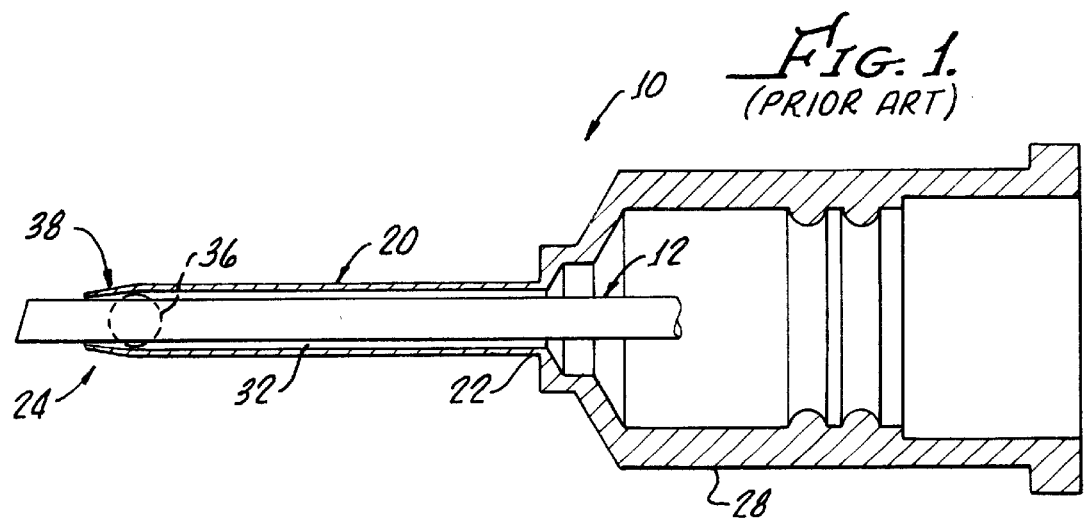
FIG. 1 cross-sectional view of prior art sleeve apparatus generally including an elongated sleeve and a hub, the sleeve having a port and is shown surrounding a phacoemulsification needle.

With reference to FIG. 1, there is shown sleeve apparatus 10 in accordance with the prior art for use with a phacoemulsification/irrigation and aspiration handpiece (not shown.) An ultrasonic drive assembly (not shown) is attached to a needle 12 for emulsifying and aspirating a cataract lens through a cornea/sclera wound (not shown).

The apparatus 10 includes an elongated sleeve 20 having a proximal end 22 and a distal end 24. The sleeve apparatus 10 may be molded from silicone and includes a hub 28 disposed at the proximal end 22 for enabling attachment of the sleeve 20 to a handpiece and orienting the needle 12 through the sleeve 20 for establishing an annular passage 32 around the needle 12 for enabling irrigation fluid to pass into an eye (not shown) through the passage 32 while cooling the needle 12. An irrigation port 36 is provided near a tip 38 of the distal end 24 for introducing irrigation fluid into the eye (not shown).

Figure 2:
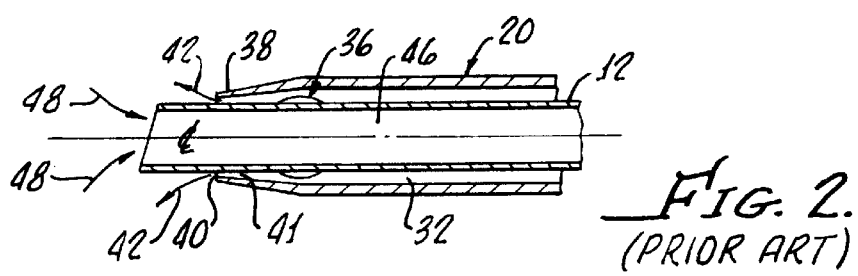
FIG. 2 is an enlarges portion of the prior art sleeve apparatus shown in FIG. 1 more clearly showing the tip portion of the sleeve.

With specific reference to FIG. 2, the sleeve 20 surrounds the needle 12 at an end point 40. Because of the small and short restricted area 41, some passage of irrigation fluid therepast, as indicated by the arrows 42, occurs. This fluid flow interferes with aspiration of fluid from the eye into a needle lumen 46 as indicated by arrows 48. Further, the distal end 24 lacks desired rigidity to withstand insertion through the wound entry of the eye.

Figure 3:
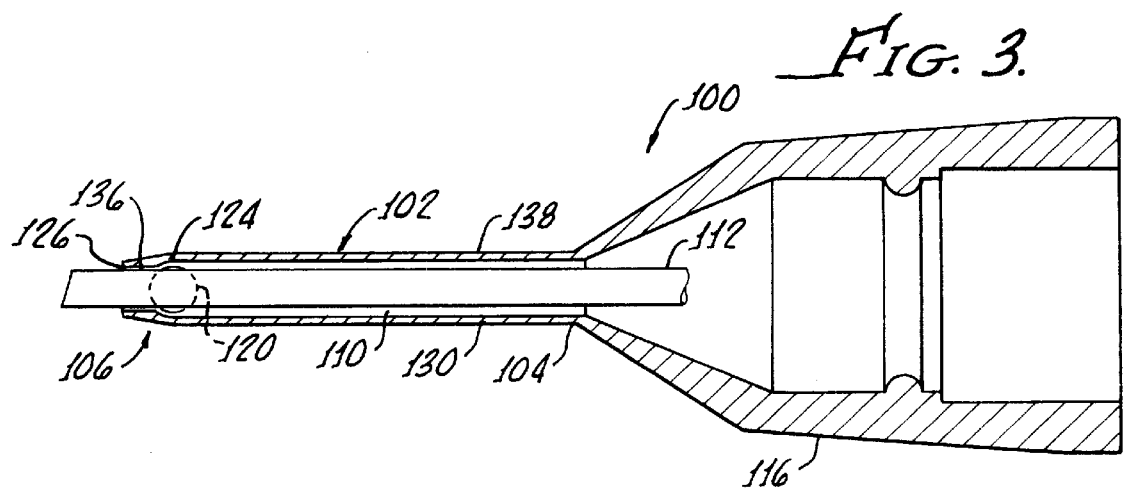
FIG. 3 is sleeve apparatus in accordance with the present invention generally showing a hub and an elongate sleeve surrounding a phacoemulsification needle.
Figure 4:
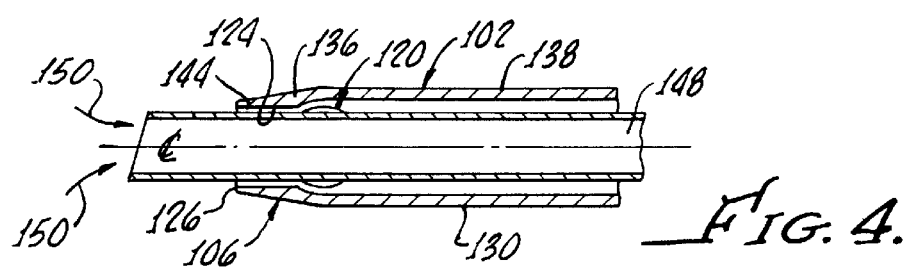
FIG. 4 is an enlargement of the tip portion of the sleeve shown in FIG. 3.

This prior art 10 is to be contrasted with the sleeve apparatus 100 in accordance with the present invention as shown in FIGS. 3 and 4. An elongate sleeve 102, which may be formed from silicone, includes a proximal end 104 and a distal end 106 with the elongate sleeve establishing an annular passage 110 around a needle 112 which enable irrigation fluid to pass into an eye through the passage 110 while cooling the needle 112. A hub 116 preferably integrally molded with the sleeve 102 is disposed at the proximal end 104 for enabling attachment of the sleeve 102 to a handpiece (not shown).

A port 120, disposed proximate the distal end 106 is provided for introducing the irrigation fluid passed through the passage 110 into an eye (not shown).

In order to provide rigidity to the distal end 106 of the elongated sleeve 102, a berm 124 is provided between the port 120 and a bitter-end 126 of the sleeve 102. Because the berm 124 portion of the sleeve has an inside diameter smaller than an inside diameter of a sleeve portion 130 extending between the port 120 and the proximate end 104, reduction of irrigation fluid therepast is significantly reduced over the prior art designs. The length of the berm 124 measured between the port 120 and the bitter-end 126 may be adjusted in order to provide limited contact with the needle 112 in order to reduce thermal transfer therebetween.

The sleeve 102 can also be considered to have a first wall thickness 136 between the port 120 and the bitter-end 126 which is greater of that the wall thickness 138 of the sleeve 102 between the port 120 and the proximal end 104.

The sleeve 102 in accordance with the present invention, because of the berm 124, or wall thickness 136, is sufficiently rigid to withstand insertion through a wound entry of an eye. Further, any gap 144 between the berm 124 and needle 112 has sufficient length to provide minimum irrigation fluid betweem the sleeve distal end 106 and the phacoemulsification needle 112. This enhances the pick-up ability of the needle 112 by enabling uninterfered flow of aspiration fluid through a needle lumen 148 as indicated by the arrows 150.

Although there has been hereinabove described, particular sleeve apparatus in accordance with the present invention for the purpose of illustrating the manner in which the invention for the purpose of illustrating the manner in which the invention may be used to advantage, it should be appreciated it is not limited thereto. Accordingly, any or all modifications, variations or equivalent arrangements which may occur to those skilled in the art, should be considered to be within the scope of the present invention as defined in the amended claims.

What is claimed is:

1. Apparatus for a phacoemulsification/irrigation and aspiration handpiece having an ultrasonic drive assembly, said apparatus comprising:

a hollow needle for emulsifying and aspirating a cataract lens through a cornea/sclera wound; and an elongated sleeve, having a proximal and distal end, the sleeve establishing an annular passage around the needle, said elongate sleeve including rigidity enhancing structure for enabling the sleeve to withstand insertion through the cornea/sclera wound and enable irrigation fluid to pass into an eye through the passage while cooling the needle, said elongate sleeve having a fixed length shorter than a length of said hollow needle thus enabling a tip of said hollow needle to protrude from said elongate sleeve, said elongate sleeve including: a hub, disposed at the proximal end, for enabling attachment of the sleeve to the handpiece; and a port, disposed proximate the distal end for introducing irrigation fluid into the eye; said rigidity enhancing structure comprising an internal continuous circumferential berm, disposed between the port and the distal end, a first constant inside diameter between the proximal end and the port and a second constant inside diameter between the port and the distal end.

* * * * *